United States Patent [19]

Allemand et al.

[11] Patent Number: 4,645,934

[45] Date of Patent: Feb. 24, 1987

[54] PROCESS FOR EXAMINING A FLAT RADIOGRAPH OF AN OBJECT AND IONIZATION CHAMBER FOR PERFORMING THE PROCESS

[75] Inventors: Robert Allemand, Saint Ismier; Jean-Jacques Gagelin, Vinay; Gaëtan Pleyber, Domene, all of France

[73] Assignee: Commissariat a l'Energie Atomique, Paris, France

[21] Appl. No.: 567,528

[22] Filed: Jan. 3, 1984

[30] Foreign Application Priority Data

Jan. 4, 1983 [FR] France .............................. 83 00034

[51] Int. Cl.$^4$ .............................................. G01T 1/18
[52] U.S. Cl. ..................................... 250/374; 250/385
[58] Field of Search .................... 250/374, 385, 363 S; 378/19, 146

[56] References Cited

U.S. PATENT DOCUMENTS

| | | | |
|---|---|---|---|
| 4,047,041 | 9/1977 | Houston | 278/19 |
| 4,383,327 | 5/1983 | Kruger | 378/99 |
| 4,392,237 | 7/1983 | Houston | 250/385 |
| 4,407,040 | 9/1977 | Houston | 250/385 |

FOREIGN PATENT DOCUMENTS

| | | |
|---|---|---|
| 0046244 | 8/1982 | European Pat. Off. . |
| 2057184 | 3/1981 | United Kingdom . |

*Primary Examiner*—Janice A. Howell
*Attorney, Agent, or Firm*—Pearne, Gordon, McCoy & Granger

[57] ABSTRACT

A process for the examination of the flat radiograph of an object irradiated with the aid of an ionizing radiation source is disclosed. In an ionization chamber is detected the latent image of the object formed by the different electrical charges produced in the volume of the chamber under the influence of the impact of the radiation flux which has traversed the object. As this irradiation is continuous, the object to be examined is moved relative to the ionization chamber in the direction and at the migration speed of the ions formed in the electrical field thereof.

1 Claim, 3 Drawing Figures

4,645,934

PROCESS FOR EXAMINING A FLAT RADIOGRAPH OF AN OBJECT AND IONIZATION CHAMBER FOR PERFORMING THE PROCESS

BACKGROUND OF THE INVENTION

The present invention relates to the examination of a radiograph of an object obtained with the aid of ionizing radiation from a source, said object having in the extent of its volume areas of variable transparency to said ionizing radiation.

In known processes of this type, the intensity of the ionizing radiation which has passed through each volume element of the object to be radiographed is generally detected by an ionization chamber in which the radiation causes electrical charges of opposite signs, whose location and intensity characterize the absorbing properties of the investigated object and constitute a latent electrical image of the thus examined object.

Thus, this latent image is formed from a certain number of electrical charges distributed in the detection volume of an ionization chamber, which is generally filled with an ionizable gas and has the property of being rapidly removed because the thus formed charges (electrons and ions), on appearance, immediately move towards the collecting electrodes of the chamber constituting the anode and cathode thereof. The problem of examining the thus obtained latent image is consequently difficult to solve, particularly as in the presently known processes it is generally necessary to work with the aid of very short ionizing radiation flashes (X, gamma or neutron rays, using a suitable converter), which correspondingly reduces the intensity of the charges produced in the volume of the chamber.

The charges created in this way by ionization produce, by influence on each electrode, charges of opposite signs and equal values, which, transformed into a detectable electrical current, immediately give an overall value of the sum of the instantaneous charges constituting the latent image. However, this unfortunately does not make it possible to achieve the desired cartography of the latent image along the OX and OY coordinates, which are respectively parallel and perpendicular to the electrical field of the chamber.

To obviate this difficulty, consideration has been given to producing ionization chambers in the form of mosaics of several juxtaposed elementary chambers, thereby making it possible to mark along the two preceding coordinates, the distribution of the space charges induced by ionization from the ionizing beam. However, the existence of partitions between the different adjacent chambers constitutes an important limitation to the accuracy of detection and also the spatial resolution of such an apparatus is obviously limited by the dimensions of the elementary volume of each detection chamber.

Consideration has also been given to the use of processes for collecting the electrical charges formed on insulating plates, so that a bidimensional latent image is obtained in this way. It is then possible to read this image by appropriate electrical devices or develope it in the manner of a photographic plate by optical reading such as that used in xerography.

In general terms, the prior art referred to hereinbefore leads to major disadvantages, which make it virtually impossible to examine the radiograph of an irradiated object with the aid of an ionization radiation source, by using as the detector an ionization chamber.

Thus, the so-called mosaic ionization chamber means have a spatial resolution, which is limited by the size of the juxtaposed elementary cells and which have a complex and therefore costly construction. The means for collecting charges on insulating plates necessarily require special devices for measuring and locating these charges on the surface and in the present state of the art these processes are extremely slow.

SUMMARY OF THE INVENTION

The present invention relates to a process for examining a radiograph of an object irradiated with the aid of an ionizing radiation source, which uses an ionization chamber and makes it possible to both form a latent image of the examined object of a very good quality and to precisely electrically examine the same using simple means.

This process for examining the radiograph of an object irradiated by means of an ionizing radiation source involves the detection in an ionization chamber of the latent image of the object formed by different electrical charges formed in the volume of the chamber under the influence of the impact of the radiation flux which has traversed the object. As the irradiation is continuous, the object to be examined is moved relative to the ionization chamber in the direction and at the migration speed of the ions formed in the electrical field thereof, so that the different latent images formed at each instant are superimposed to give a single image, which is consequently enriched through further new informations, by moving at the speed of the ions towards the collecting electrode. The X and Y coordinates of each point of the image are deduced, for the x coordinate corresponding to the displacement direction of the object, from the arrival time of the corresponding charge on the collecting electrode, and for the perpendicular y coordinate from the location of the impact of the same charge on the collecting electrode.

Thus, as a result of the displacement of the irradiated object at the speed of the ions relative to the chamber, and to the continuous irradiation of the object to be examined, it is possible to concentrate the different informations appearing over a period of time on the transparency of this object into a single latent image which, by definition, moves at the same time as the object. The fact that there is only a single latent image which remains the same during the displacement of the object, makes it possible to obtain this X or gamma ray image in real time and obviate all the disadvantages resulting in the prior art from the fact that the response of an ionization chamber is not uniform as a function of the appearance point of each of the charges, because it is well known that the resolving power of an ionization chamber deteriorates with the increase in the distance from the point of appearance of a charge and the collecting electrode. However, according to the process of the invention, as there is a single latent image moving at the speed of the ions formed, it is possible to a certain extent to reestablish the uniformity of the chamber response, because the exposure time of the system corresponds to the displacement time of the latent image or the object and this applies to all the patterns of the image.

Moreover, it is relatively easy to move the object to be examined at the ion migration rate, because in a standard ionization chamber filled e.g. with xenon gas, said ion migration rate is approximately 100 cm/s, which approximately corresponds to the walking speed of man. This ion velocity of speed V is also a function of three parameters, namely the mobility $\mu_c$, the electrical field E prevailing between the anode and the cathode, and the pressure P of the filling gas in accordance with the formula:

$$V = \mu_c(E/P)$$

Thus, by acting on the electrical field E or the pressure P, it is easily possible to regulate the speed of the ions and, according to the invention, it is even possible, if necessary, to make the displacement speed of the object dependent on the aforementioned speed of the ions.

Finally, it must be borne in mind and which is obvious to the expert, that the displacement of the object relative to the ionization chamber is to be considered as a relative displacement, which means that it remains within the scope of the present invention to move the chamber relative to the fixed object at the ion migration rate.

The present invention also relates to an ionization chamber for performing the aforementioned process and which, in per se known manner, comprises a flat anode and a flat cathode, which face one another in an ionizable gas atmosphere. The chamber comprises, raised to an intermediate potential between those of the anode and the cathode, a screen grid located in the immediate vicinity of the ion-collecting electrode. The collecting electrode is subdivided, in the direction of the y coordinate perpendicular to the field, into several adjacent sectors raised to the same potential, but which are mechanically independent of one another.

As a result of the aforementioned ionization chamber structure, it is possible to simultaneously realise two different objectives which will be explained thereinafter.

Firstly, by placing in the ionization chamber, a screen grid which is as close as possible to the ion-collecting electrode, the space of the chamber is subdivided into two unequal volumes, namely a volume for detecting the information carried by the ionization radiation flux and corresponding to the space between the screen grid and the non-collecting electrodes. There is also a very small volume for reading this information, which corresponds to that part of the chamber between the screen grid and the ion-collecting electrode. The function of the screen grid is to form a true electrostatic screen, which makes it possible to electrostatically separate the two aforementioned spaces, i.e. the reading space is only influenced by the charges located there as a result of their migration, thereby excluding most of them, which are formed in the much larger detection space between the screen grid and the non-collecting electrode. According to the invention, the screen grid is in the immediate vicinity of the ion-collecting electrode, i.e. also mechanically as close as possible thereto. The optimum achievable distance is e.g. a few tenths of a mm. This same screen grid is raised to an intermediate potential between that of the anode and that of the cathode of the chamber. This potential is chosen experimentally or by calculation, as a function of the grid shape. This leads to compatibility between the electrostatic screen function fulfilled by it and its relatively good transparency to the ions, which it must obviously not collect in an excessively large number by preventing them from migrating from the detection space towards the reading space.

The second feature adopted by the ionization chamber according to the invention is of having an ion-collecting electrode, which is usually the cathode, which is subdivided in direction OY, perpendicular to the migration of the ions, into several parallel adjacent sectors at the same electrical potential, but which are materially independent of one another. This ensures a detection of the location of each electrical charge, in accordance with the space coordinate OY parallel to the plane of the collecting electrode. According to the realisation of the process according to the invention, the latent image of the irradiated object moves at the same speed as the object and consequently this makes it possible, on the basis of the arrival time of a given charge in the narrow reading band between the screen grid and the collecting electrode, to determine the space coordinate of said same charge in the direction OX of the electrical field of the chamber, i.e. in the ion migration direction.

Finally, according to the invention, the ionization chamber can have any desirable shape, as a function of the radiation source used and the spatial distribution thereof. For example, it can have a generally parallelepipedic shape, when the source is sufficiently remote, the radiation flux then reaching the object to be studied with a relative parallelism. It is also possible for it to have a spherical or cylindrical symmetry centred on the point source, when the latter is less remote, which then leads to the adoption of a cradle shape for the ionization volume.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
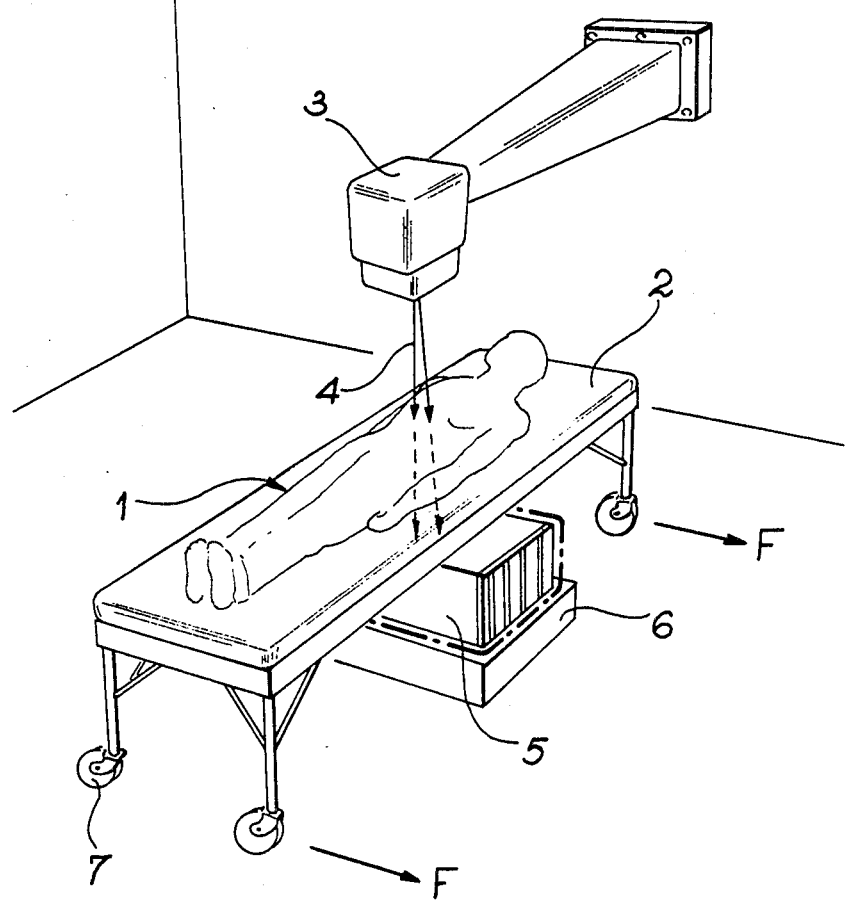
FIG. 1 an application of the radiograph examination process according to the invention applied to the radiography of the human body.

FIG. 1 shows in exemplified manner an application of the process for examining the radiograph of an object irradiated by ionizing radiation, in which the object is a patient 1 stretched out on a mobile table or bed 2. It is obvious that this example is given as a non-limitative, illustrative embodiment of one of the possible applications of the process according to the invention. However, the latter applies in general terms to the radiography of a random object, in view of the fact that it has a variable transparency characterizing its internal structure which is to be examined, compared with a X, gamma or neutron ionizing radiation flux.

In FIG. 1, a source 3 of ionizing radiation 4 irradiates the patient 1 and a radiograph is read beneath the bed 2 by an ionization chamber 5, fixed to the ground by means of a base 6. According to the invention, the bed 2 supporting the patient is mobile by means of a system of rollers 7 in the direction of the arrows F corresponding to that of the electrical field of the ionization chamber 5 at the migration rate of the ions formed in the detection space of chamber 5, under the action of the radiation 4 which has passed through the patient's body.

The practical means for moving bed 2 on rollers 7 are not specifically shown in FIG. 1, but it is obvious that such means are well known to the expert and, in particular, a per se known control system can bring about the necessary synchronism between the speed of movement of bed 2 and the ion migration rate in ionization chamber 5.

Figure 2:
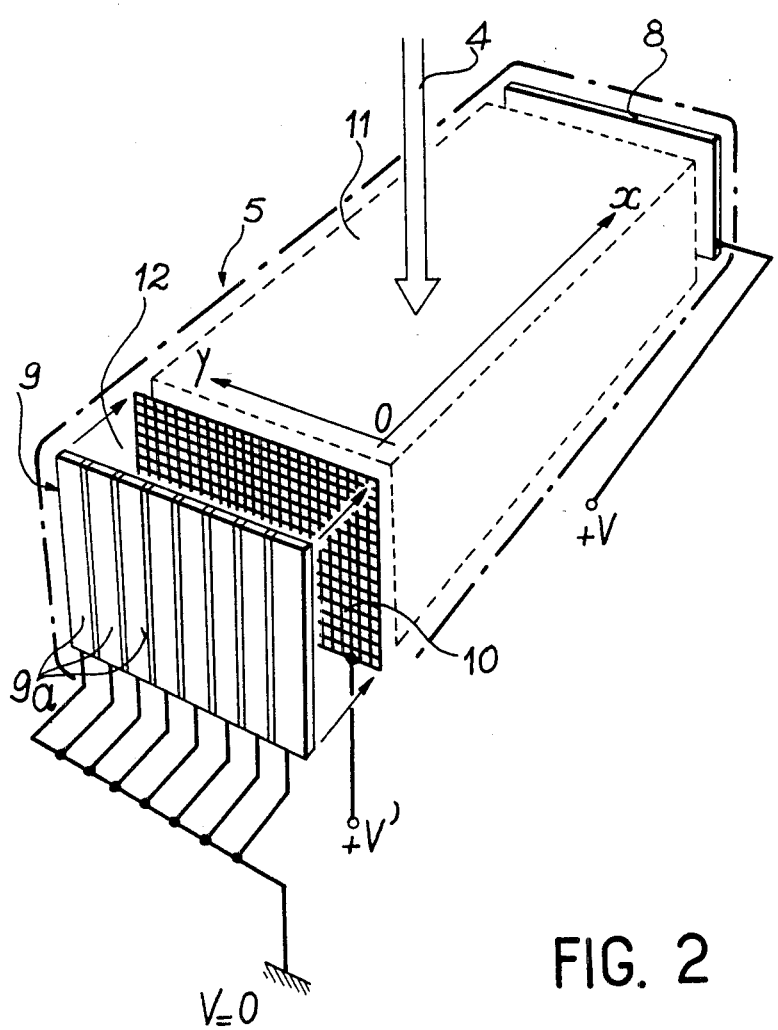
FIG. 2 the structure of an ionization chamber according to the invention in a parallelepipedic geometrical configuration.

FIG. 2 diagrammatically shows an ionization chamber for performing the process according to the invention in a parallelepipedic structure. This ionization chamber has an anode 8 raised to potential $+V$ and a cathode 9 raised to the potential of the ground and constituted according to the invention by the juxtapositioning of a series of collecting electrodes 9a, all raised to the same potential, but which are materially independent of one another. This special construction of cathode 9 leads to a partitionless juxtapositioning in ionization chamber 5 of a certain number of elementary chambers, whose number is equal to that of the collecting electrodes 9a.

According to the invention, chamber 5 also has a screen grid 10 raised to a potential $V'$ intermediate between that of anode 8 and that of cathode 9 and located a few tenths of a mm from the latter. In a preferred embodiment of chamber 5, the internal space thereof is filled with xenon gas and the potentials $V$ and $V'$ are respectively $+2500V$ and $+400V$, the space between screen grid 10 and the collecting electrodes 9a being 4/10 mm. The screen grid 10 is formed by a netting of metal wires arranged in two perpendicular directions.

According to the invention, screen grid 10 subdivides the internal space of chamber 5 into two different areas, namely a first area or detection space 11 between screen grid 10 and anode 8, and a second area or reading space 12 between screen grid 10 and collecting electrodes 9a. Thus, from the electrostatic standpoint, the two spaces 11 and 12 are completely separate, so that each of them can fulfill a different function. Thus, space 11 subject to the ionizing radiation flux 4, indicated by an arrow in FIG. 2, corresponds to the detection space, i.e. where in per se known manner ionizing radiation 4 produces, by ionization of the xenon gas contained in chamber 5, pairs of positive ions and electrons of equal, but opposite charges, which immediately migrate in direction OX of the electrical field towards cathode 9 and anode 8. The reading space 12 is shown in greatly enlarged form in FIG. 2 for ease of viewing purposes, because it in fact only takes up a few tenths of a millimeter. In reading space 12, the charges which have migrated from space 11 are detected by influence on the various electrodes 9a as they pass through the screen grid 10. The appearance of an electrical signal on one of these sectoral electrodes 9a makes it possible to determine the coordinate OY perpendicular to the electrical field of the chamber 5 corresponding to the thus detected charge.

Figure 3:
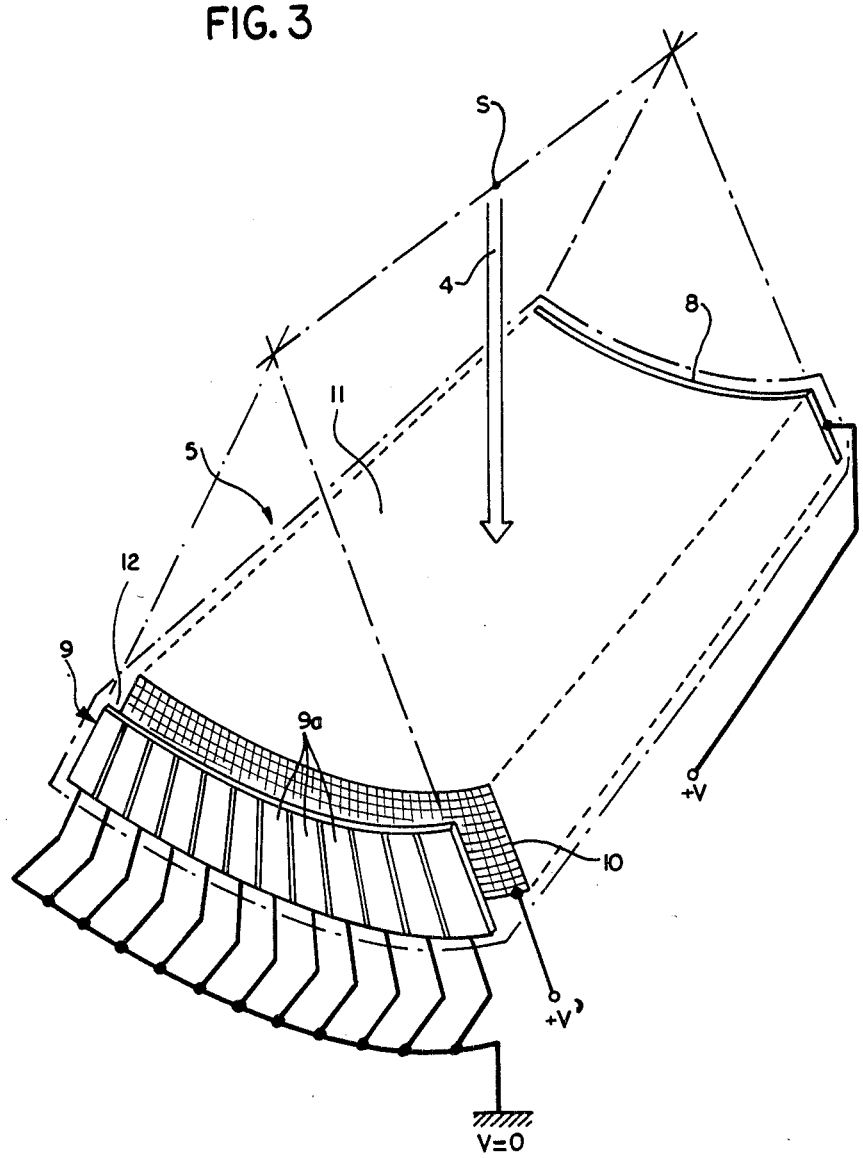
FIG. 3 a cradle-shaped ionization chamber according to the invention.

FIG. 3 shows an ionization chamber 5 according to the invention, but which has a cradle-like shape with a cylindrical symmetry, whose centre is the quasi-point source S of the ionizing radiation 4. In the embodiment of FIG. 3, the same structural elements are encountered, with the exception of the shape, as those in FIG. 2 and are provided with the same reference numerals.

The aforementioned ionization chambers according to the invention have important advantages, particularly great constructional simplicity and low cost for a very high resolving power and precision.

In its main utilization as taking the image of the projection of an object irradiated by a point gamma or X radiation source, the invention offers a system having high measuring dynamics and a very good response uniformity. In addition, the ionization chambers according to the invention have a low geometrical distortion factor resulting from the quasi-parallelism of the trajectories of the ions in the detection medium of the chamber.

Among the interesting applications of the present application, reference is made to continuous digital gamma or X electroradiography and particularly the inspection of objects on an endless conveyor belt (checking luggage in airports for example), or in linear tomography.

What is claimed is:

1. A process for the examination of a flat radiograph of an object comprising the steps of providing an ionizing radiation source of the type in which detection on a collecting electrode of the latent image of the object formed takes place in an ionization chamber by the different electrical charges produced in the volume of the chamber under the influence of the impact of the radiation flux which has traversed the object; producing an electrical field between an anode and a cathode at opposite ends of said chamber to establish an ion migration speed; deducing a latent image along X and Y coordinates, with the X coordinate corresponding to the direction of ion migration produced by said electrical field in said chamber and to the displacement direction of the object from the arrival time of the corresponding charge on the collecting electrode, said ion migration being at a substantially constant and continuous speed, and with the perpendicular Y coordinate corresponding to the displacement of the object from the location of impact of the same charge on the collecting electrode; continuously irradiating the object; and moving the object relative to the ionization chamber in the direction of the X coordinate and at a speed equal to the constant and continuous migration speed of the ions formed in the electrical field thereof, to thereby superimpose the different instantaneous latent images into a single image.

* * * * *